(12) United States Patent  
Sakuragi

(10) Patent No.: US 9,808,145 B2  
(45) Date of Patent: Nov. 7, 2017

(54) VIRTUAL ENDOSCOPIC IMAGE GENERATION DEVICE, METHOD, AND MEDIUM CONTAINING PROGRAM

(71) Applicant: FUJIFILM Corporation, Tokyo (JP)

(72) Inventor: Futoshi Sakuragi, Tokyo (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 329 days.

(21) Appl. No.: 14/662,441

(22) Filed: Mar. 19, 2015

(65) Prior Publication Data

US 2015/0190038 A1     Jul. 9, 2015

Related U.S. Application Data

(63) Continuation of application No. PCT/JP2013/005495, filed on Sep. 18, 2013.

(30) Foreign Application Priority Data

Sep. 26, 2012   (JP) .................................. 2012-211643

(51) Int. Cl.
  *H04N 13/00*   (2006.01)
  *A61B 1/00*    (2006.01)
  (Continued)

(52) U.S. Cl.
  CPC ........ *A61B 1/00193* (2013.01); *A61B 1/0005* (2013.01); *A61B 1/00009* (2013.01);
  (Continued)

(58) Field of Classification Search
  CPC ..... A61B 1/00009; A61B 1/0005; A61B 6/12; A61B 8/0841; G06T 19/20; G06T 2210/41; G06T 2219/2012; G06K 9/468
  See application file for complete search history.

(56) References Cited

U.S. PATENT DOCUMENTS

| 2002/0128547 A1 | 9/2002 | Furuhashi et al. |
| 2011/0242097 A1* | 10/2011 | Miyamoto ............. G06T 15/08 345/419 |

(Continued)

FOREIGN PATENT DOCUMENTS

| EP | 2 554 104 A1 | 2/2013 |
| JP | 2000-90283 A | 3/2000 |

(Continued)

OTHER PUBLICATIONS

Communication dated May 23, 2016 from the European Patent Office in counterpart Application No. 13841974.2.

(Continued)

*Primary Examiner* — Sath V Perungavoor  
*Assistant Examiner* — Peet Dhillon  
(74) *Attorney, Agent, or Firm* — Sughrue Mion, PLLC

(57) ABSTRACT

A structure extracting unit extracts a structure from a three-dimensional medical image, and a view point determining unit determines a view point position and a direction of line of sight of a virtual endoscopic image. An image generating unit calculates a distance between the view point position and the extracted structure, changes an opacity defined in a color template depending on the distance, and generates, from the three-dimensional medical image, a virtual endoscopic image containing the structure shown according to the color template with the changed opacity viewed from the view point position in the direction of line of sight. A display control unit displays the thus generated virtual endoscopic image on a WS display.

6 Claims, 7 Drawing Sheets

(51) Int. Cl.
*G06T 19/20* (2011.01)
*G06K 9/46* (2006.01)
*G06T 19/00* (2011.01)
*H04N 13/02* (2006.01)
*A61B 6/12* (2006.01)
*A61B 8/08* (2006.01)

(52) U.S. Cl.
CPC ............ *G06K 9/468* (2013.01); *G06T 19/006* (2013.01); *G06T 19/20* (2013.01); *H04N 13/0203* (2013.01); *A61B 6/12* (2013.01); *A61B 8/0841* (2013.01); *G06T 2207/10068* (2013.01); *G06T 2210/41* (2013.01); *G06T 2219/2012* (2013.01)

(56) References Cited

U.S. PATENT DOCUMENTS

| | | | |
|---|---|---|---|
| 2012/0113111 A1* | 5/2012 | Shiki | A61B 8/08 345/419 |
| 2013/0018255 A1 | 1/2013 | Kitamura et al. | |
| 2013/0023730 A1 | 1/2013 | Kitamura et al. | |

FOREIGN PATENT DOCUMENTS

| | | |
|---|---|---|
| JP | 2000149062 A | 5/2000 |
| JP | 2002-263053 A | 9/2002 |
| JP | 2003-91735 A | 3/2003 |
| JP | 2009-261519 A | 11/2009 |
| JP | 2010-220742 A | 10/2010 |
| JP | 2011-212244 A | 10/2011 |
| JP | 2011-212245 A | 10/2011 |
| JP | 2011-212314 A | 10/2011 |
| JP | WO 2011122037 A1 * | 10/2011 ......... A61B 1/00009 |
| WO | 2011/122037 A1 | 10/2011 |

OTHER PUBLICATIONS

Jun Masumoto et al., "Automated Liver Segmentation Method for Dynamic CT Data Using Non-Rigid Registration", Journal of Computer Aided Diagnosis of Medical Images, Jun. 2003, pp. 29-38, vol. 7, No. 1-4.

Puteri Suhaiza Sulaiman et al., "A Liver Level Set (LLS) Algorithm for Extracting Liver's Volume Containing Disconnected Regions Automatically", International Journal of Computer Science and Network Security (IJCSNS), Dec. 2008, pp. 246-252, vol. 8, No. 12.

Takeshi Hitosugi et al., "Development of a liver extraction method using a level set method and its performance evaluation", Journal of Computer Aided Diagnosis of Medical Images, Jun. 2003, pp. 1-9, vol. 7, No. 4-2.

International Search Report for PCT/JP2013/005495 dated Nov. 26, 2013.

Communication dated Oct. 13, 2015 from the Japanese Patent Office in counterpart application No. 2012-211643.

* cited by examiner

ID GENERATION DEVICE, METHOD, AND
MEDIUM CONTAINING PROGRAM

VIRTUAL ENDOSCOPIC IMAGE GENERATION DEVICE, METHOD, AND MEDIUM CONTAINING PROGRAM

CROSS-REFERENCE TO RELATED APPLICATIONS

This application is a Continuation of PCT International Application No. PCT/JP2013/005495 filed on Sep. 18, 2013, which claims priority under 35 U.S.C. §119(a) to Japanese Patent Application No. 2012-211643 filed on Sep. 26, 2012. Each of the above applications is hereby expressly incorporated by reference, in its entirety, into the present application.

BACKGROUND OF THE INVENTION

Technical Field

The present invention relates to a device, a method, and a program for generating a virtual endoscopic image that shows the interior of a body cavity of a subject for assisting endoscopic observation during surgery, examination etc., using an endoscope inserted into the body cavity of the subject.

Background Art

Endoscopic surgeries, such as laparoscopic surgery and thoracoscopic surgery, are drawing attention in recent years. The endoscopic surgery has an advantage in that the burden imposed on the patient is quite small since it can be conducted by forming only a few incisions of several centimeters for inserting an endoscope and a surgical tool, without requiring laparotomy or thoracotomy. On the other hand, conducting a surgery under a limited field of view of the endoscope is highly difficult in view of skill and requires a highly-skilled operating surgeon. If a blood vessel or an organ of the patient is erroneously damaged and bleeds during an endoscopic surgery, the manner of surgery has to be changed to one using a conventional technique involving laparotomy or thoracotomy.

On the other hand, a virtual endoscope technique for generating an image that is similar to an endoscopic image from a three-dimensional volume image obtained by imaging with a CT apparatus, or the like, is known. This technique is popular in North America as a method for finding a tumor, in particular, a tumor in the large intestine by CT imaging without performing an endoscopic examination. Further, a technique for safely and quickly performing an endoscopic surgery, examination, or the like, using a virtual endoscopic image is proposed.

For example, Japanese Unexamined Patent Publication No. 2002-263053 (hereinafter, Patent Document 1) teaches a device that detects the position of the endoscope with a sensor to determine the detected position as a view point, generates a virtual endoscopic image having a wider angle of view than that of the endoscope, and displays a real endoscopic image obtained by endoscopic imaging and the virtual endoscopic image superimposed one on the other.

However, although the technique taught in Patent Document 1 allows compensating for the narrow field of view of the endoscope with a virtual endoscopic image, the virtual endoscopic image has the same view point and the same observation direction as those of the real endoscopic image, and a part of interest, such as a target of surgery, may not be shown in the virtual endoscopic image or the real endoscopic image depending on the positional relationship between the part of interest and the endoscope, making it difficult to understand the positional relationship between the endoscope and the part of interest.

In order to address this problem, Japanese Unexamined Patent Publication No. 2011-212245 (hereinafter, Patent Document 2), for example, proposes a technique where a color template for changing the color of a virtual endoscopic image depending on the distance from the view point position of a virtual endoscope is defined for each structure, and the color of each structure is changed depending on the distance from the view point. Further, Japanese Unexamined Patent Publication No. 2011-212244 (hereinafter, Patent Document 3) proposes a technique where a color template defining an opacity for each structure to display a semi-transparent image of each part, in order to prevent such a situation that a structure of interest is not shown when another structure is present between the view point position of a virtual endoscope and the structure of interest. According to the technique taught in Patent Document 3, the structure of interest can be seen in a virtual endoscopic image even when another structure is present between the view point position of the virtual endoscope and the structure of interest.

SUMMARY OF INVENTION

The technique taught in Patent Document 3, however, applies the color template defining an opacity to display a semi-transparent image to all the structures, and all the structures, including the structure of interest, contained in the virtual endoscopic image are shown as semi-transparent images. This may make it difficult to see the structure of interest.

In view of the above-described circumstances, the present invention is directed to allow appropriately making a structure visible depending on a distance between the structure and a view point position of a virtual endoscope.

A virtual endoscopic image generation device according to the invention comprises: image obtaining means for obtaining a three-dimensional image of a subject containing a plurality of structures; structure extraction means for extracting at least one structure from the three-dimensional image; view point determination means for determining a virtual view point position and a virtual direction of line of sight in a body cavity of the subject; storing means for storing a display attribute defined for each of the plurality of structures, the display attribute defining an opacity that is changed depending on a distance from the view point position; and image generation means for changing the opacity defined in the display attribute of the extracted structure depending on a distance between the view point position and the extracted structure, and generating, from the three-dimensional image, a virtual endoscopic image containing the extracted structure having the display attribute with the changed opacity viewed from the view point position in the direction of line of sight.

Specific examples of the "structure" as used herein include a part to undergo endoscopic surgery, and an anatomic structure that needs special attention during surgery, such as a blood vessel, an organ, a tumor, etc. A specific method for identifying the position of such a structure may be an automatic method using a known image recognition technique, a method involving manual operation by the user, or a combination of the automatic method and the manual method.

The "display attribute" as used herein may include, besides the opacity, a color template that is defined such that a virtual endoscopic image showing each part having almost the same appearance as the part in a body cavity shown in the real endoscopic image is obtained. The display attribute may further include information about whether the structure is shaded or not, and the type of light source, such as ambient light or diffused light.

In the virtual endoscopic image generation device according to the invention, the opacity may be changed such that the opacity is 0 when the distance is equal to or greater than a first threshold value and equal to or smaller than a second threshold value, and the opacity is 1 when the distance is equal to a third threshold value between the first and the second threshold values.

In the virtual endoscopic image generation device according to the invention, the image generation means may calculate a shortest distance between the view point position and the extracted structure.

In the virtual endoscopic image generation device according to the invention, the image generation means may calculate a distance between the view point position and a centroid of the extracted structure.

The virtual endoscopic image generation device according to the invention may further comprise display control means for displaying the virtual endoscopic image on display means.

A virtual endoscopic image generation method according to the invention comprises: obtaining a three-dimensional image of a subject containing a plurality of structures; extracting at least one structure from the three-dimensional image; determining a virtual view point position and a virtual direction of line of sight in a body cavity of the subject; and changing, depending on a distance between the view point position and the extracted structure, an opacity defined in a display attribute defined for each of the plurality of structures, the display attribute defining the opacity that is changed depending on a distance from the view point position, and generating, from the three-dimensional image, a virtual endoscopic image containing the extracted structure having the display attribute with the changed opacity viewed from the view point position in the direction of line of sight.

The invention may be provided in the form of a program for causing a computer to carry out the virtual endoscopic image generation method according to the invention.

According to the virtual endoscopic image generation device and method of the invention, a three-dimensional image of a subject containing a plurality of structures is obtained, at least one structure is extracted from the three-dimensional image, and a virtual view point position and a virtual direction of line of sight in a body cavity of the subject are determined. Then, an opacity defined in a display attribute, which is defined for each of the plurality of structure and defines the opacity that is changed depending on a distance from the view point position, is changed depending on a distance between the view point position and the extracted structure. Then, a virtual endoscopic image containing the structure having the display attribute with the changed opacity is generated from the three-dimensional image. This allows changing the opacity of the structure depending on the distance from the view point position, such that the opacity of the structure is 0 when it is excessively far from or close to the view point position, and the opacity of the structure is 1 when it is at an appropriate distance for observation. In this manner, the structure can appropriately be made visible depending on the view point position and the direction of line of sight of the virtual endoscope.

DESCRIPTION OF PREFERRED EMBODIMENTS

Figure 1:
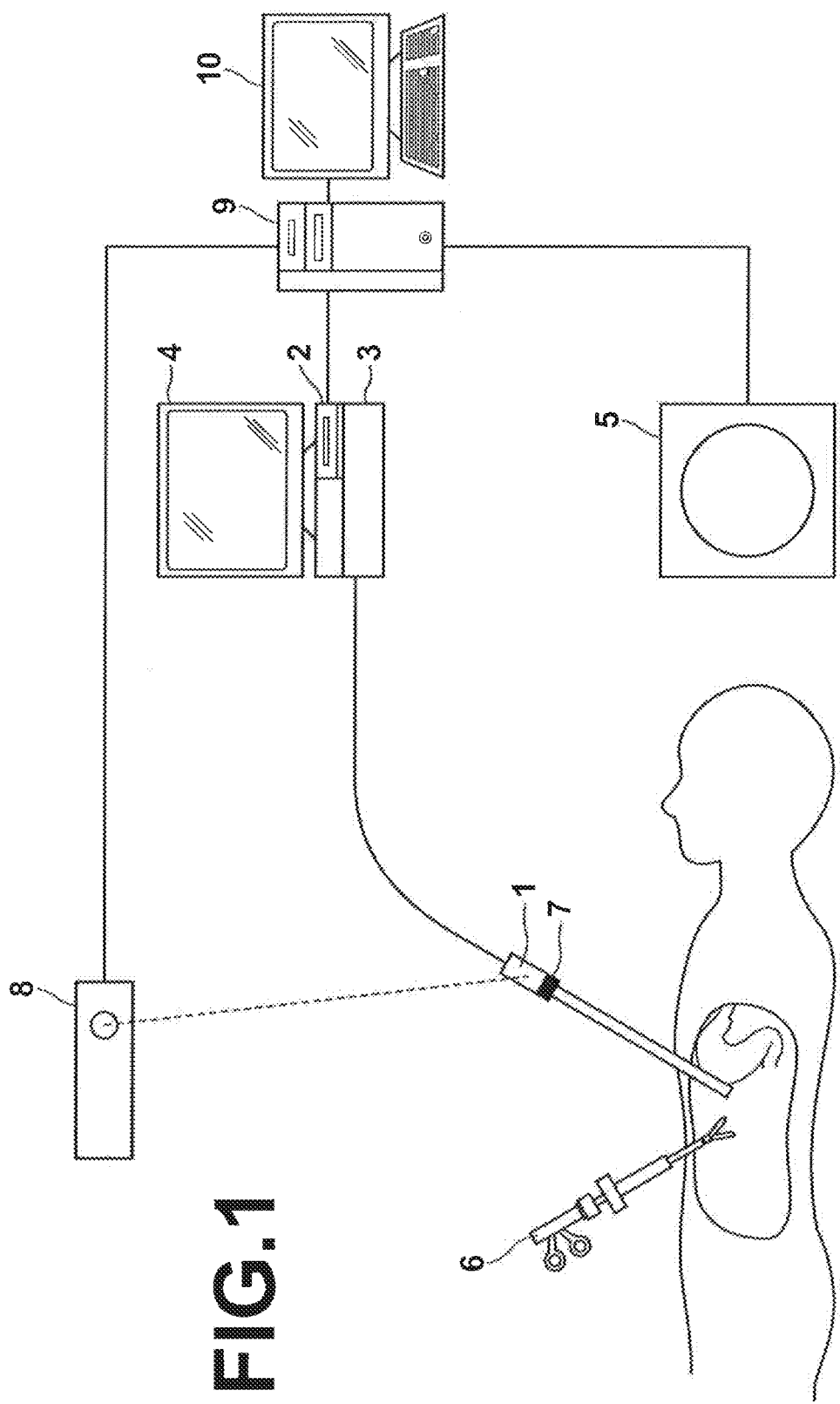
FIG. 1 is a diagram illustrating the hardware configuration of an endoscopic observation assisting system to which a virtual endoscopic image generation device according to an embodiment of the invention is applied.

Hereinafter, an embodiment of the present invention will be described with reference to the drawings. FIG. 1 is a diagram illustrating the hardware configuration of an endoscopic observation assisting system to which a virtual endoscopic image generation device according to an embodiment of the invention is applied. As shown in FIG. 1, this system includes an endoscope 1, a digital processor 2, a light source unit 3, a real endoscopic image display 4, a modality 5, a surgical tool 6, an endoscope marker 7, a position sensor 8, an image processing workstation 9, and an image processing workstation display (which will hereinafter be referred to as "WS display") 10.

The endoscope 1 of this embodiment is a rigid endoscope for abdominal cavity, and is inserted in the abdominal cavity of a subject. Light from the light source unit 3 is guided through optical fibers and is outputted from the distal end of the endoscope 1 to illuminate the abdominal cavity, and an image of the interior of the abdominal cavity of the subject is obtained by an imaging optical system of the endoscope 1. The digital processor 2 converts an imaging signal obtained by the endoscope 1 into a digital image signal and performs image quality corrections by digital signal processing, such as white balance adjustment and shading correction. Then, the digital processor 2 adds associated information defined by the DICOM (Digital Imaging and Communications in Medicine) standard to the processed signal to output real endoscopic image data G0. The outputted real endoscopic image data G0 is sent to the image processing workstation 9 via a LAN according to a communication protocol conforming to the DICOM standard. Further, the digital processor 2 converts the real endoscopic image data G0 into an analog signal and outputs the analog signal to the real endoscopic image display 4, and the real endoscopic image G0 is displayed on the real endoscopic image display 4. The image signal is obtained by the endoscope 1 at a predetermined frame rate, and the real endoscopic image G0 displayed on the real endoscopic image display 4 is a moving image showing the interior of the abdominal cavity. The endoscope 1 is also capable of taking a still image in response to a user's operation.

The modality 5 images a part to be examined of the subject and generates image data M of a three-dimensional medical image showing the part. In this example, the modality 5 is a CT apparatus. The three-dimensional medical image data M is also provided with associated information defined by the DICOM standard. The three-dimensional medical image data M is also sent to the image processing workstation 9 via the LAN according to the communication protocol conforming to the DICOM standard.

The endoscope marker 7 and the position sensor 8 form a known three-dimensional position measurement device. The endoscope marker 7 is disposed in the vicinity of the grip of the endoscope 1, and the optical position sensor 8 detects the three-dimensional position of the marker 7 at predetermined time intervals. The endoscope marker 7 is formed by a plurality of marker pieces, which enable the position sensor 8 to detect the orientation of the endoscope 1 based on the positional relationships among the marker pieces. The orientation of the endoscope 1 as used herein refers to the orientation in which the endoscope is inserted. The orientation of the endoscope 1 is the same as the orientation of the line of sight at the center of the field of view of the endoscope, and may hereinafter be referred to as the orientation or the central line of sight vector of the endoscope 1. A three-dimensional position (detected endoscope position) P0 of the distal end of the endoscope 1 can be calculated by offset calculation. The position sensor 8 sends three-dimensional position data indicating the calculated view point position P0 of the endoscope 1 and three-dimensional orientation data indicating a orientation D0 to the image processing workstation 9 via a USB interface.

The image processing workstation 9 is a computer having a known hardware configuration including a CPU, a main storage unit, an auxiliary storage unit, an input-output interface, a communication interface, a data bus, etc., and has an input device (such as a pointing device, a keyboard, etc.) and the WS display 10 connected thereto. The image processing workstation 9 is connected to the digital processor 2 and the modality 5 via the LAN, and is connected to the position sensor 8 via a USB connection. The image processing workstation 9 has a well-known operating system and various software applications installed thereon, which include an application for executing an endoscopic observation assisting process of this embodiment. These software applications may be installed from a recording medium, such as a CD-ROM, or may be downloaded from a storage unit of a server connected via a network, such as the Internet, before being installed.

Figure 2:
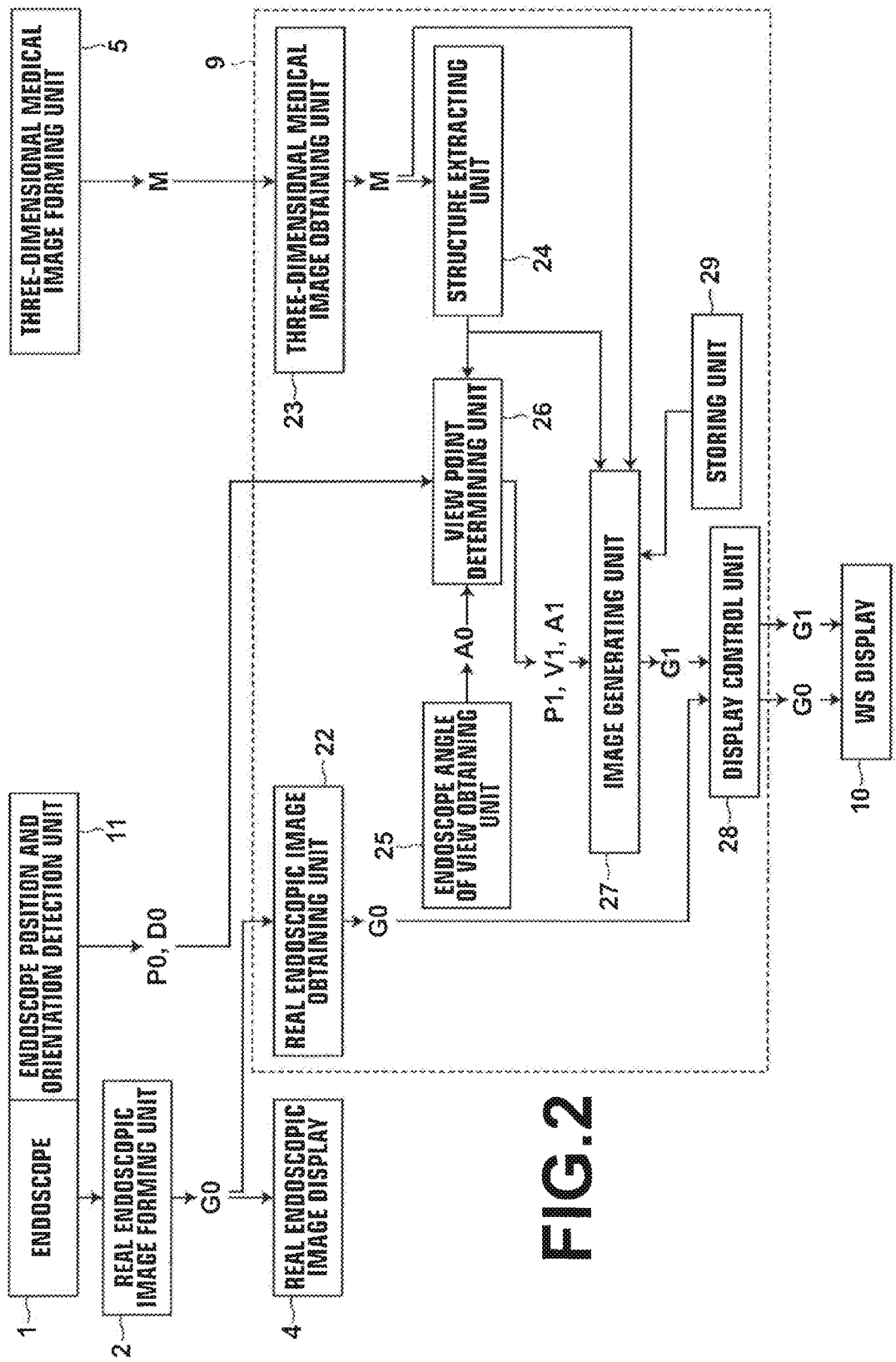
FIG. 2 is a functional block diagram of the endoscopic observation assisting system according to an embodiment of the invention.

FIG. 2 is a block diagram showing functional blocks of the endoscopic observation assisting system according to an embodiment of the invention. As shown in FIG. 2, the endoscopic observation assisting system according to this embodiment includes the endoscope 1, a real endoscopic image forming unit 2, the real endoscopic image display 4, a three-dimensional medical image forming unit 5, the WS display 10, an endoscope position and orientation detection unit 11, a real endoscopic image obtaining unit 22, a three-dimensional medical image obtaining unit 23, a structure extracting unit 24, an endoscope angle of view obtaining unit 25, a view point determining unit 26, an image generating unit 27, a display control unit 28, and a storing unit 29.

It should be noted that a functional block shown in FIG. 2 that generally corresponds one to one to one of the hardware devices shown in FIG. 1 is denoted by the same symbol as that of the corresponding hardware device shown in FIG. 1. Namely, the function of the real endoscopic image forming unit 2 is implemented by the digital processor shown in FIG. 1, and the function of the three-dimensional medical image forming unit 5 is implemented by the modality shown in FIG. 1. On the other hand, the function of the endoscope position and orientation detection unit 11 is implemented by the endoscope marker 7 and the position sensor 8. The dashed line frame denotes the image processing workstation 9. The function of each unit shown within the dashed line frame is implemented by executing a predetermined program on the image processing workstation 9. A real endoscopic image G0, a detected endoscope position P0, an endoscope orientation D0, an endoscope angle of view A0, a view point position P1 of a virtual endoscope, a central line of sight vector V1 of the virtual endoscope, an angle of view A1 of the virtual endoscope, a three-dimensional medical image M, and a virtual endoscopic image G1 are data that are written in and read from predetermined memory areas of the image processing workstation 9 by each unit shown within the dashed line frame.

Next, the schematic flow of user's operations performed on the endoscopic observation assisting system of this embodiment and operations performed by the above-described units of the endoscopic observation assisting system are described with reference to the flow chart shown in FIG. 3.

First, prior to observation of the interior of the abdominal cavity of a subject with the endoscope 1, the three-dimensional medical image forming unit 5 images the interior of the abdominal cavity of the subject to form a three-dimensional medical image M. On the image processing workstation 9, the three-dimensional medical image obtaining unit 23 obtains the three-dimensional medical image M formed by the three-dimensional medical image forming unit 5 (step ST1). Then, the structure extracting unit 24 presents a user interface for receiving a user's operation specifying a structure (such as a target of surgery) in the body cavity shown in the three-dimensional medical image M. The structure extracting unit 24 having received the user's operation specifying a structure extracts the specified structure from the three-dimensional medical image M (step ST2). It should be noted that the number of structure(s) to be specified and extracted may be one or two or more.

Figure 3:
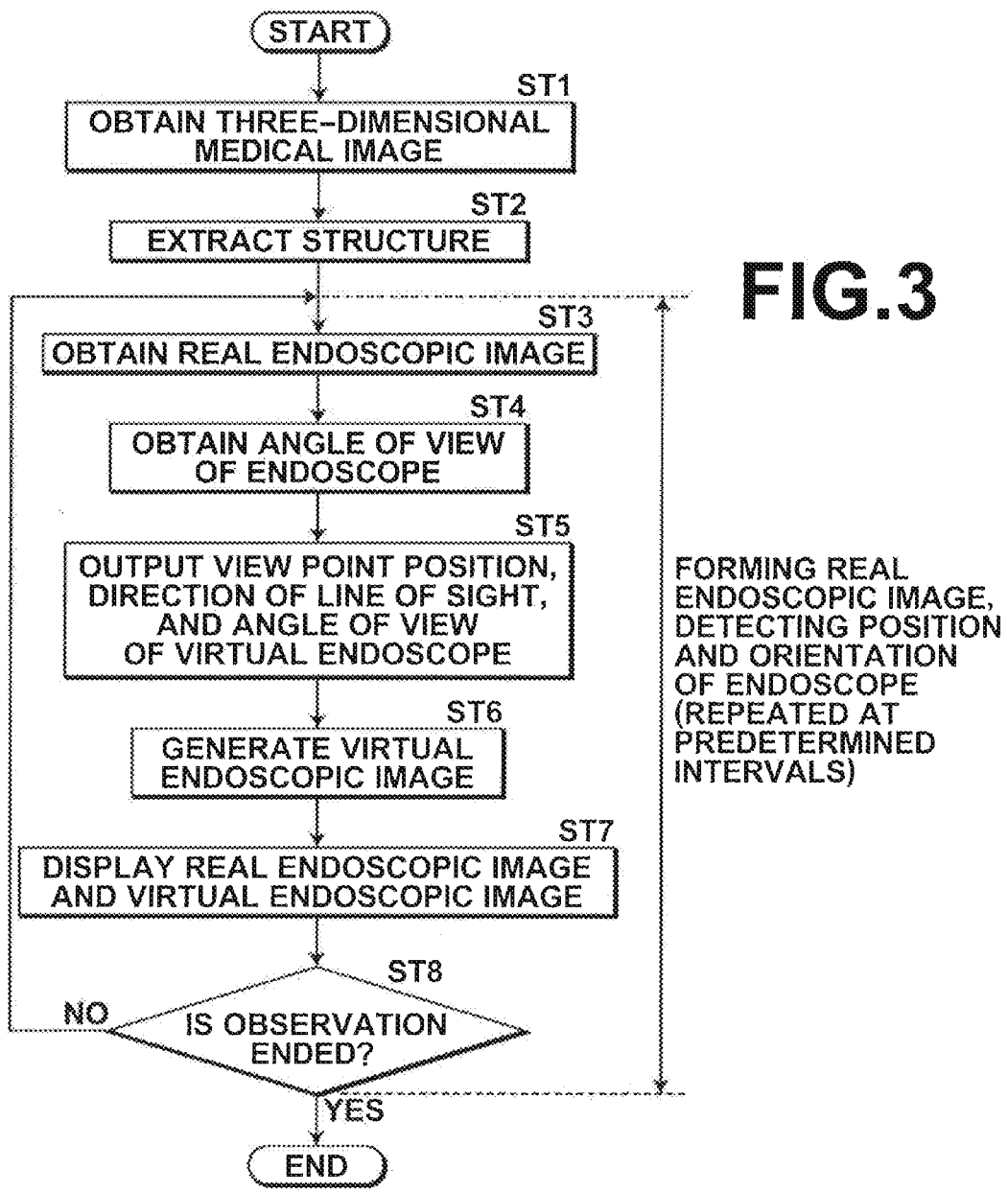
FIG. 3 is a flow chart illustrating the flow of an endoscopic observation assisting process according to the embodiment.

During endoscopic surgery, i.e., during observation of the interior of the abdominal cavity of the subject with the endoscope 1, the real endoscopic image forming unit 2 repeatedly forms a real endoscopic image G0 that is imaged with the endoscope 1 inserted in the body cavity at a predetermined frame rate, and the thus formed real endoscopic image G0 is displayed real-time as a live view image on the real endoscopic image display 4 until the observation ends (that is, when the determination in step ST8 is "YES"), as noted on the right of the flow chart shown in FIG. 3. Also, the endoscope position and orientation detection unit 11 repeatedly detects the real-time position P0 and the real-time orientation D0 of the endoscope 1 inserted in the body cavity at predetermined time intervals.

On the image processing workstation 9, the real endoscopic image obtaining unit 22 obtains the real endoscopic image G0 formed by the real endoscopic image forming unit 2 (step ST3), and the endoscope angle of view obtaining unit 25 obtains the angle of view A0 of the endoscope 1 from a predetermined memory area in the image processing workstation 9 (step ST4). At almost the same timing as the operations in steps ST3 and ST4, the view point determining unit 26 obtains the detected endoscope position P0 and the orientation D0 detected by the endoscope position and orientation detection unit 11, and converts the obtained endoscope position P0 and orientation D0 into a position and an orientation in a coordinate system of the three-dimensional medical image M to obtain a view point position P1 and a direction of line of sight (central line of sight vector) V1 of the virtual endoscope. Further, the view point determining unit 26 determines, based on the view point position P0, the orientation D0, and the angle of view A0, a virtual field of view of the virtual endoscope positioned in the view point position P1 such that the virtual field of view has continuity with an endoscope-corresponding field of view, which is a field of view in the three-dimensional medical image corresponding to the field of view of the endoscope 1, and outputs the view point position P1, the direction of line of sight V1, and the angle of view A1 of the virtual endoscope (step ST5).

When the three-dimensional medical image M obtained by the three-dimensional medical image obtaining unit 23 is inputted to the image generating unit 27, the image generating unit 27 generates a virtual endoscopic image G1 having the virtual field of view viewed from the view point (P1) corresponding to the endoscope position P0, based on the view point position P1, the central line of sight vector V1, and the angle of view A1 of the virtual endoscope determined by the view point determining unit 26 (step ST6).

Then, the display control unit 28 displays the real endoscopic image G0 obtained by the real endoscopic image obtaining unit 22 and the virtual endoscopic image G1 generated by the image generating unit 27 on the WS display 10 (step ST7).

On the image processing workstation 9, the operations in steps ST3 to ST7 are repeated while no operation instructing to end the observation is made (when the determination in step ST8 is "NO"). In this manner, temporally-synchronized successive display of the real endoscopic images G0 and the virtual endoscopic images G1 on the WS display 10 is achieved. When an operation instructing to end the observation is made (when the determination in step ST8 is "YES"), the image processing workstation 9 ends the process.

Next, detailed operations performed by the individual units in the image processing workstation 9 are described.

The real endoscopic image obtaining unit 22 is a communication interface that communicates with the real endoscopic image forming unit (digital processor) 2 to receive a real endoscopic image G0 and stores the received real endoscopic image G0 in a predetermined memory area in the image processing workstation 9. The real endoscopic image G0 is transferred from the real endoscopic image forming unit 2 in response to a request from the real endoscopic image obtaining unit 22.

The three-dimensional medical image obtaining unit 23 has a communication interface function to receive the three-dimensional medical image M from the three-dimensional medical image forming unit 5 and store the received three-dimensional medical image M in a predetermined memory area in the image processing workstation 9.

The structure extracting unit 24 presents, on a cross-sectional image showing a given cross-section, which is generated from the three-dimensional medical image M using the well-known MPR technique, a user interface for receiving a user's operation specifying a structure of interest via the pointing device or keyboard of the image processing workstation 9. For example, when a structure shown in the cross-sectional image is clicked on with the pointing device, the structure extracting unit 24 extracts the structure specified by the click operation from the three-dimensional medical image M and stores the extracted structure in a predetermined memory area in the image processing workstation 9.

As the structure, a target of surgery, a part that needs special attention during surgery, etc., may be specified, as desired by the user. For example, in a case where the three-dimensional medical image M is obtained by imaging the abdomen of a subject, the body surface, the liver, the portal vein in the liver, the kidneys, etc., may be specified by the user and extracted from the three-dimensional medical image M.

To extract the body surface, the liver, and the kidneys, any technique can be used, such as estimating a range of CT values where each of the body surface, the liver, and the kidneys is found in the three-dimensional medical image M, and performing thresholding using the values to thereby apply a morphology filter to an extracted region. Examples of techniques that can be used to extract, in particular, the liver include: a technique taught in J. Masumoto et al., "Automated Liver Segmentation Method for Dynamic CT Data Using Non-Rigid Registration", Journal of Computer Aided Diagnosis of Medical Images, Vol. 7, No. 4-1, pp. 29-38, 2003, which involves detecting a contrast enhanced pattern of the liver region by using a plurality of liver phase images taken in time order, and extracting the liver region by using the detected pattern; and a level set method taught in P. S. Sulaiman et al., "A Liver Level Set (LLS) Algorithm for Extracting Liver's Volume Containing Disconnected Regions Automatically", IJCSNS International Journal of Computer Science and Network Security, Vol. 8, No. 12, pp. 246-252, 2008, and T. Hitosugi et al., "Development of a liver extraction method using a level set method and its performance evaluation", Journal of Computer Aided Diagnosis of Medical Images, Vol. 7, No. 4-2, pp. 1-9, 2003.

Examples of the technique that can be used to extract the portal vein include: a technique taught in Japanese Unexamined Patent Publication No. 2010-220742, which involves calculating positional information and a principal axis direction of a plurality of candidate points representing a tissue of interest formed by a line-like structure, and performing reconstruction to connect the candidate points to each other using a cost function with a variable based on the calculated positional information and the calculated principal axis direction; and a technique taught in Japanese Unexamined Patent Publication No. 2011-212314, which automatically distinguishes and extracts blood vessels.

It should be noted that the structures may be extracted by manual operation by the user.

The endoscope angle of view obtaining unit 25 obtains information about the angle of view A0 of the endoscope 1, which is set in advance in startup parameters of the program, a setting file, etc., based on specifications of the endoscope 1. In a case where the information of the angle of view A0 of the endoscope 1 is included in the associated information added to the real endoscopic image G0, the endoscope angle of view obtaining unit 25 may obtain the information about the angle of view A0 of the endoscope 1 by analyzing the associated information.

The view point determining unit 26 has a function of a communication interface for communicating with the endoscope position and orientation detection unit 11 to obtain the detected endoscope position P0 and the orientation D0, and a function of converting the obtained detected endoscope position P0 and orientation D0, which are in the three-dimensional coordinate system of the position sensor 8, into the view point position P1 and the direction of line of sight (central line of sight vector) V1 of the virtual endoscope which are expressed by coordinate values in the three-dimensional coordinate system of the three-dimensional medical image M, and storing the view point position P1 and the direction of line of sight (central line of sight vector) V1 of the virtual endoscope in predetermined memory areas of the image processing workstation 9. With the former communication interface function, the detected endoscope position P0 and the orientation D0 are obtained from the endoscope position and orientation detection unit 11 in response to a request from the view point determining unit 26.

With the latter coordinate conversion function, based on a correspondence relationship between the orientation of each coordinate axis of the three-dimensional coordinate system of the position sensor and the orientation of each coordinate axis of the three-dimensional coordinate system of the three-dimensional medical image M, an amount of rotation of the coordinate axes is found in advance, and a coordinate value of a position on the subject in the three-dimensional coordinate system of the position sensor 8 corresponding to the origin of the three-dimensional medical image M is measured in advance. Then, based on the coordinate value of the origin, an amount of translation between these coordinate axes is found. Then, using a matrix that performs rotation by the amount of rotation and translation by the amount of translation, conversion of the detected endoscope position P0 and the orientation D0 expressed in the three-dimensional coordinate system of the position sensor 8 into the view point position P1 and the direction of line of sight (central line of sight vector) V1 of the virtual endoscope expressed by coordinate values in the three-dimensional coordinate system of the three-dimensional medical image M can be achieved.

Figure 4:
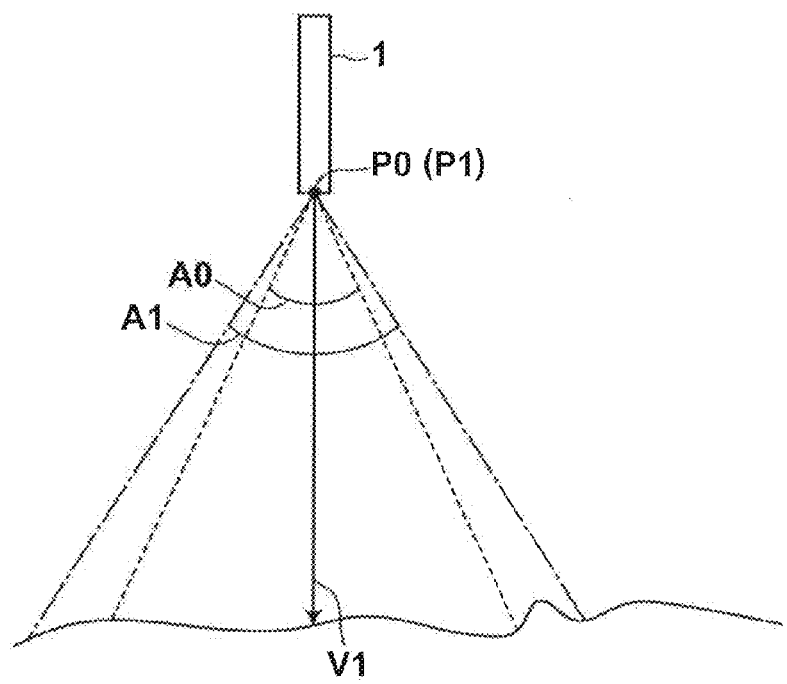
FIG. 4 is a diagram schematically showing one example of a field of view of a virtual endoscope, which is determined based on a field of view of a real endoscope and the position of a structure according to the embodiment.

In this manner, the view point position and the orientation of the central line of sight vector of the virtual endoscope are aligned with those of the endoscope 1, as schematically shown in FIG. 4. That is, the detected endoscope position P0 obtained by the endoscope position and orientation detection unit 11 is determined as the view point position P1 of the virtual endoscope, and the core line direction of the endoscope 1 which is based on the orientation D0 of the endoscope 1 obtained by the endoscope position and orientation detection unit 11 is determined as the direction of line of sight (central line of sight vector) V1 of the virtual endoscope.

Further, the view point determining unit 26 determines the angle of view A1 of the virtual endoscope which is wider than the angle of view A0 of the endoscope 1. Specifically, when the angle of view A0 is θ, the angle of view A1 of the virtual endoscope can be calculated by adding a constant to greater one of the angle of view A0 of the endoscope 1 and 2θ, or multiplying greater one of the angle of view A0 of the endoscope 1 and 2θ with a predetermined factor greater than 1. The thus determined view point position P1, the central line of sight vector V1, and the angle of view A1 of the virtual endoscope are written in predetermined memory areas.

When the three-dimensional medical image M is inputted to the image generating unit 27, the image generating unit 27 sets the orientation of the central line of sight vector V1 of the virtual endoscope as the orientation of the line of sight vector passing through the center of the field of view, as shown in FIG. 4, and sets a plurality of lines of sight that radially extend from the view point position P1 of the virtual endoscope within the range of angle of view A, to generate a virtual endoscopic image G1 by projecting pixel values along each line of sight using the well-known volume rendering involving central projection. The volume rendering is performed with using a color template that defines colors and transparency levels in advance such that an image showing each part having almost the same appearance as that of the corresponding part in the abdominal cavity shown in the real endoscopic image G0 is obtained. Further, whether the structures are shaded or not, and the type of light source, such as ambient light or diffused light, may be defined as display attributes, together with the color template. It should be noted that the color template or the display attributes are stored in the storing unit 29.

Figure 5:
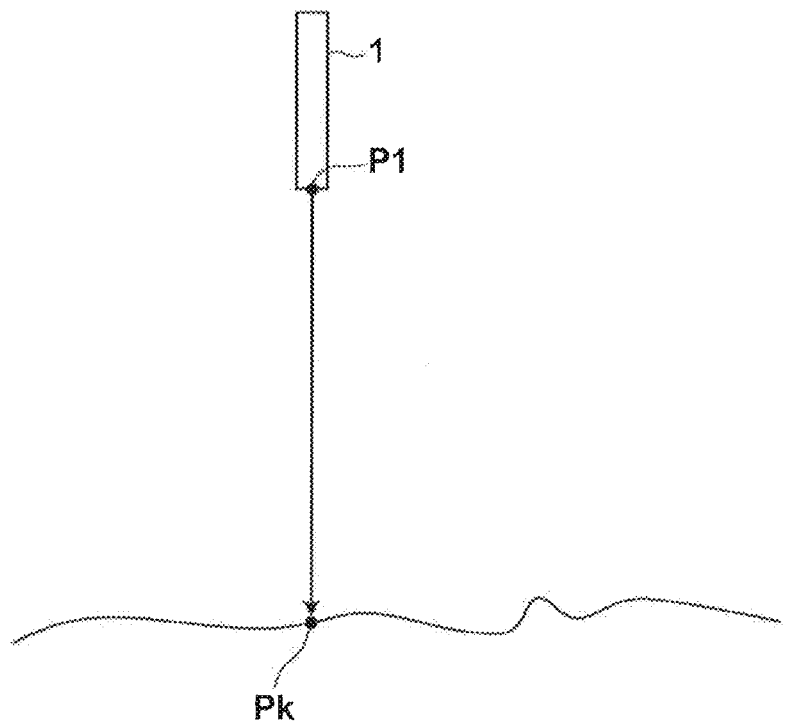
FIG. 5 is a diagram for explaining how a distance between a view point position of a virtual endoscope and a structure is calculated.

In this embodiment, the opacity of each structure is defined to be changed depending on a distance from the view point position P1 to the structure. The distance from the view point position P1 to each structure is the shortest distance between the view point position P1 and the surface of the structure along the direction of line of sight V1. Specifically, as shown in FIG. 5, when an intersection point Pk between a straight line extending from the view point position P1 along the direction of line of sight V1 and the surface of the structure is set, a distance from the view point position P1 to the intersection point Pk on the three-dimensional medical image M is the distance from the view point position P1 to the structure.

Figure 6:
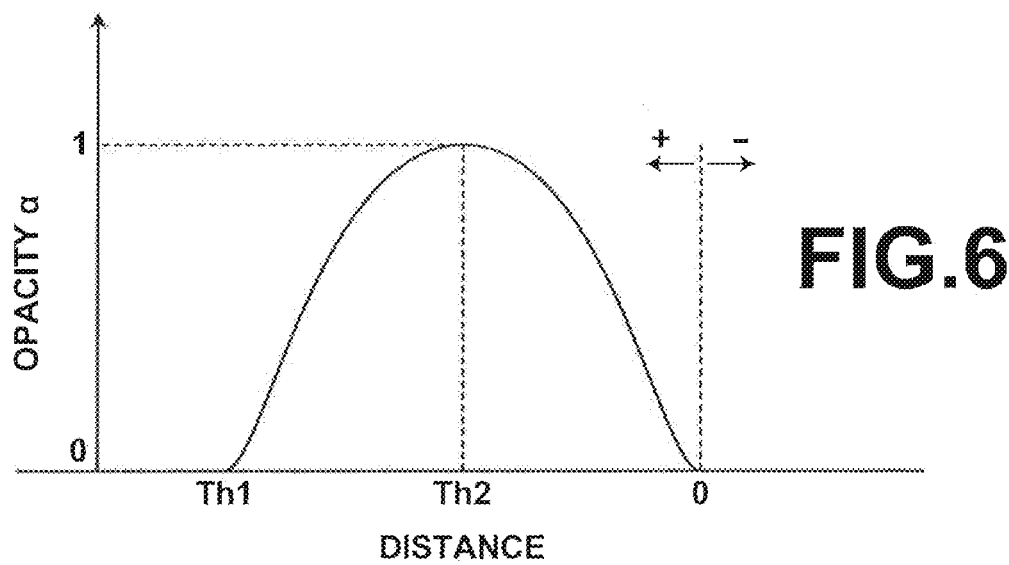
FIG. 6 shows an opacity depending on a distance defined in a color template.
Figure 7:
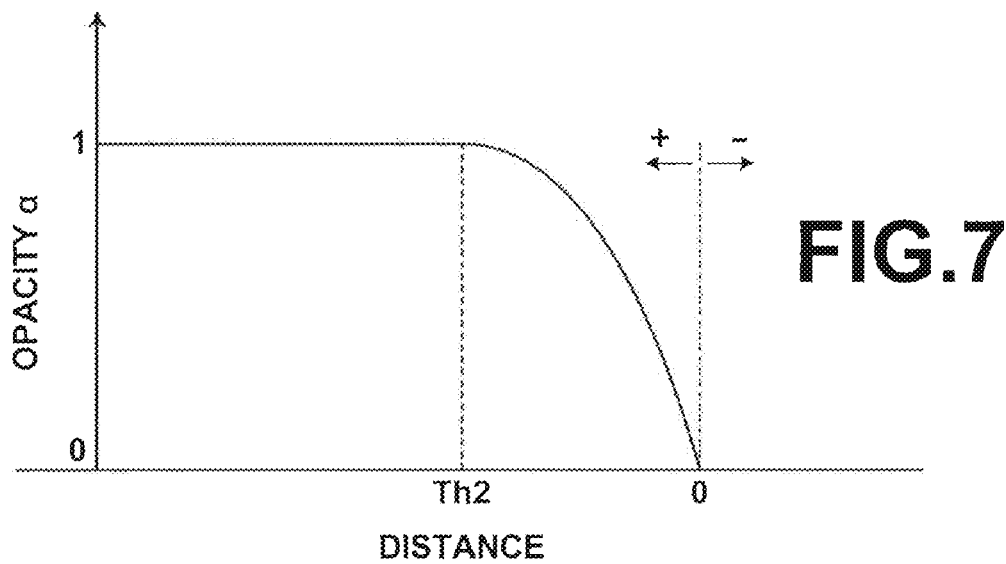
FIG. 7 shows an opacity depending on a distance defined in a color template.

FIG. 6 shows a relationship between the distance and the opacity. In FIG. 6, the horizontal axis represents the distance between the view point position P1 and a structure, where a direction in which the distance increases is indicated by "+", and a direction in which the distance decreases is indicated by "−". As shown in FIG. 6, when the distance between the view point position P1 and the structure is equal to or greater than a threshold value Th1, the opacity α is 0, and the opacity α gradually increases as the distance between the view point position P1 and the structure decreases, and the opacity α is 1 when the distance between the view point position P1 and the structure is equal to a threshold value Th2. Then, when the distance between the view point position P1 and the structure further decreases, the opacity α gradually decreases, and the opacity α is 0 when the view point position P1 reaches the structure and the distance between the view point position P1 and the structure is 0. It should be noted that, when the view point position P1 is moved further from the structure, the opacity α of the structure remains 0. The opacity α depending on the distance may be changed in a high-order curve fashion, as shown in FIG. 6, or may be changed linearly. Further, the manner of changing the opacity α may be changed depending on the type of the structure. For example, if the structure is a body surface, the opacity α may be 1 when the distance between the view point position P1 and the structure is equal to or greater than the threshold value Th2, as shown in FIG. 7.

By defining the relationship between the distance and the opacity α in this manner, structures included in the virtual endoscopic image are provided with different opacities α depending on the view point position P1, and visibility of each structure shown in the displayed virtual endoscopic image G1 is changed depending on the distance from the view point position P1. FIGS. 8 to 11 are diagrams for explaining visibility of each structure depending on the view point position P1. In FIGS. 8 to 11, three structures K1 to K3 in order from a body surface K0 are shown inside the body surface K0, where the distance between the view point position P1 of the virtual endoscopic image and the structure K0 to K3 shown in the solid line in each drawing is assumed to be equal to the threshold value Th2 shown in FIG. 6. Further, in FIGS. 8 to 11, the solid line indicates a structure that is opaque, and the dashed line indicates a structure that is transparent.

Figure 8:
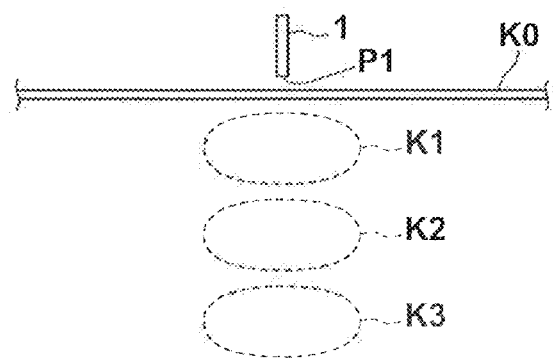
FIG. 8 is a diagram for explaining visibility of each structure depending on the view point position.

First, as shown in FIG. 8, when the view point position P1 of the virtual endoscopic image is outside the body surface K0, the virtual endoscopic image contains only the body surface K0. In this state, the structures K1 to K3 are transparent, and are not visible in the virtual endoscopic image. When the view point position P1 is moved from this state and the distance between the view point position P1 and the body surface K0 is less than the threshold value Th2, the body surface K0 gradually becomes transparent as the view point position P1 is moved closer to the body surface K0. Then, when the view point position P1 reaches the body surface K0, the opacity of the body surface K0 is 0 and the body surface K0 is transparent, and the body surface K0 is not visible in the virtual endoscopic image.

Figure 9:
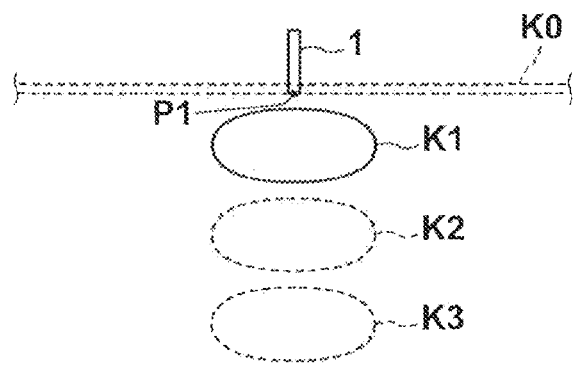
FIG. 9 is a diagram for explaining visibility of each structure depending on the view point position.

Then, as shown in FIG. 9, when the view point position P1 passes through the body surface K0 and is moved closer to the structure K1, the opacity α of the structure K1, which has been transparent and invisible until then, gradually increases. When the distance between the view point position P1 and the structure K1 is equal to the threshold value Th2, the structure K1 is fully visible in the virtual endoscopic image. In this state, the body surface K0 and the structures K2 and K3 are transparent and are invisible in the virtual endoscopic image. When the view point position P1 is moved from this state and the distance between the view point position P1 and the structure K1 becomes less than the threshold value Th2, the structure K1 gradually becomes transparent as the view point position P1 is moved closer to the structure K1. Then, when the view point position P1 reaches the structure K1, the opacity of the structure K1 is 0 and the structure K1 is transparent, and the structure K1 is invisible in the virtual endoscopic image.

Figure 10:
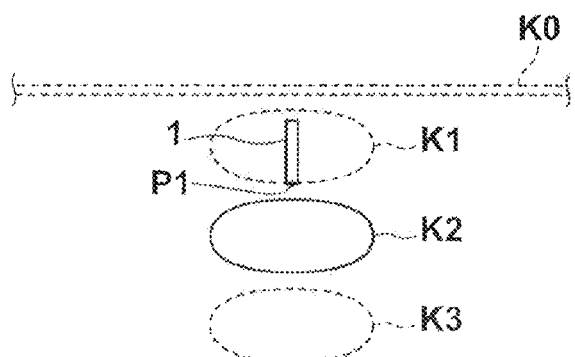
FIG. 10 is a diagram for explaining visibility of each structure depending on the view point position.

Then, as shown in FIG. 10, when the view point position P1 passes through the structure K1 and is moved closer to the structure K2, the opacity α of the structure K2, which has been transparent and invisible until then, gradually increases. When the distance between the view point position P1 and the structure K2 is equal to the threshold value Th2, the structure K2 is fully visible in the virtual endoscopic image. In this state, the body surface K0 and the structures K1 and K3 are transparent and are invisible in the virtual endoscopic image. When the view point position P1 is moved from this state and the distance between the view point position P1 and the structure K2 becomes less than the threshold value Th2, the structure K2 gradually becomes transparent as the view point position P1 is moved closer to the structure K2. Then, when the view point position P1 reaches the structure K2, the opacity of the structure K2 is 0 and the structure K2 is transparent, and the structure K2 is invisible in the virtual endoscopic image.

Figure 11:
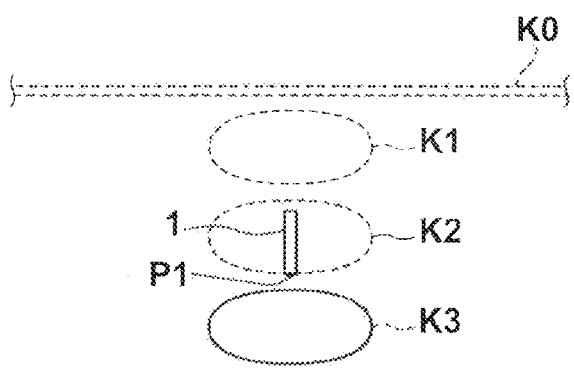
FIG. 11 is a diagram for explaining visibility of each structure depending on the view point position, FIG. 12 schematically shows one example of a real endoscopic image and a virtual endoscopic image displayed side by side according to the embodiment.

Then, as shown in FIG. 11, when the view point position P1 passes through the structure K2 and is moved closer to the structure K3, the opacity α of the structure K3, which has been transparent and invisible until then, gradually increases. When the distance between the view point position P1 and the structure K3 is equal to the threshold value Th2, the structure K3 is fully visible in the virtual endoscopic image. In this state, the body surface K0 and the structures K1 and K2 are transparent and are invisible in the virtual endoscopic image. When the view point position P1 is moved from this state and the distance between the view point position P1 and the structure K3 becomes less than the threshold value Th2, the structure K3 gradually becomes transparent as the view point position P1 is moved closer to the structure K3. Then, when the view point position P1 reaches the structure K3, the opacity of the structure K3 is 0 and the structure K3 is transparent, and the structure K3 is invisible in the virtual endoscopic image.

Figure 12:
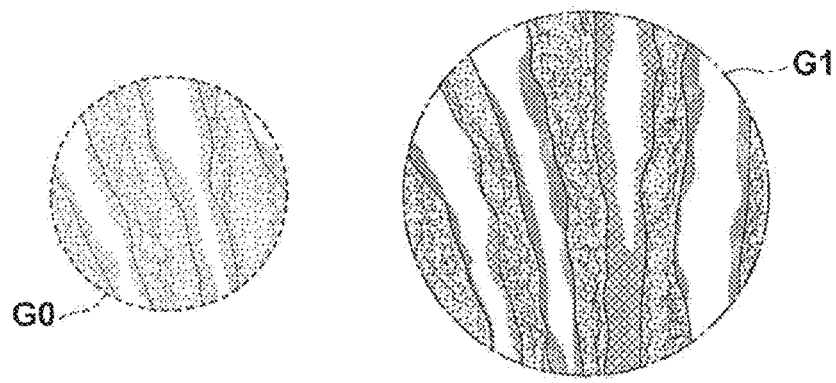

The display control unit 28 generates a display screen on which the real endoscopic image G0 and the virtual endoscopic image G1 are shown side by side, and outputs the generated display screen to the WS display 10. Thus, the display screen on which the real endoscopic image G0 and the virtual endoscopic image G1 are shown side by side, as shown in FIG. 12, is displayed on the WS display 10. It should be noted that the real endoscopic image G0 and the virtual endoscopic image G1 may be displayed with being superimposed one on the other, as taught in Patent Document 3, using the well-known alpha blending, or the like.

As described above, in this embodiment, a structure is extracted from a three-dimensional medical image M of a subject containing a plurality of structures, and the virtual view point position P1 and the virtual line of sight direction V1 in the body cavity of the subject are determined. Then, the opacity of the extracted structure is changed depending on the distance between view point position P1 and the structure, and a virtual endoscopic image G1 showing the structure with the changed opacity is generated from the three-dimensional medical image M. This allows changing the opacity of the structure depending on the distance from the view point position, such that the opacity of the structure is 0 when it is excessively far from or close to the view point position, and the opacity of the structure is 1 when it is at an appropriate distance for observation. In this manner, the structure can appropriately be made visible depending on the view point position P1 of the virtual endoscope.

It should be noted that the manner of changing the opacity in the above-described embodiment, as shown in FIGS. 6 and 7, is not intended to limit the invention. For example, the opacity may be changed such that the opacity α of the structure gradually increases while the view point position is moved closer to the position of the structure, and the opacity α is 1 when the view point position reaches the position of the structure, and then the opacity α of the structure becomes 0 or gradually decreases to 0 after the view point position has passed through the position of the structure.

Further, although the view point position and the direction of line of sight of the virtual endoscopic image are aligned with those of the real endoscopic image in the above-described embodiment, a user's specification of the view point position and the direction of line of sight may be received on a displayed MPR image or a volume rendered image, for example, which is generated from the three-dimensional medical image M. In this case, the specified view point position and the specified direction of line of sight are in the coordinate system of the three-dimensional medical image M, and can be used as the view point position P1 and the direction of line of sight V1 for generating a virtual endoscopic image.

Figure 13:
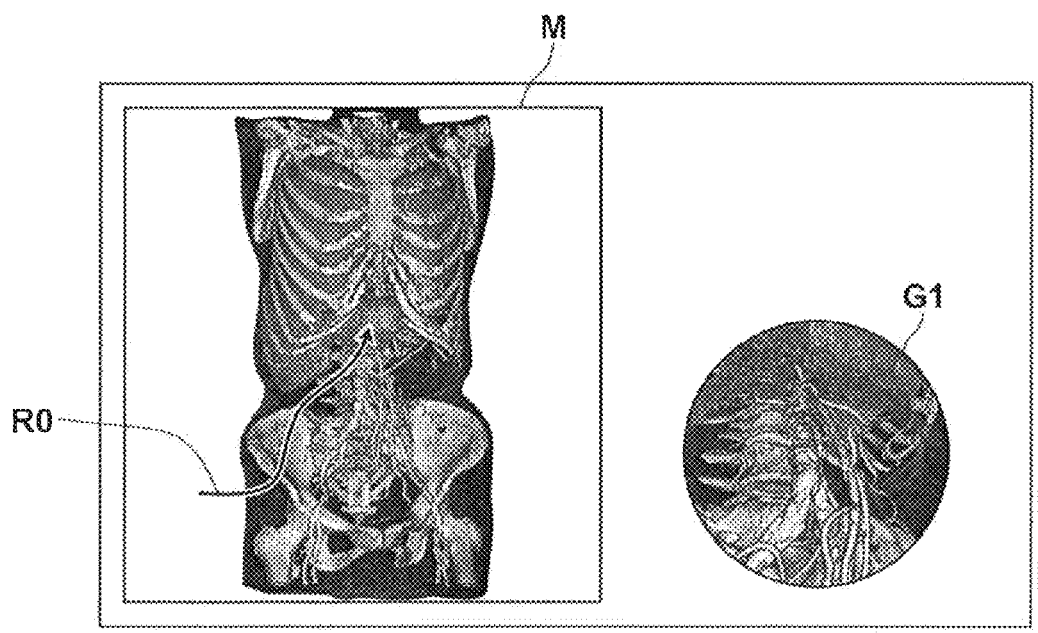
FIG. 13 shows a state where a route of an endoscope is set in a three-dimensional medical image.

In this case, as shown in FIG. 13, the three-dimensional medical image M and a route R0 of the endoscope set in the three-dimensional medical image M may be displayed, and a virtual endoscopic image G1 viewed from the view point position P1 in the direction of line of sight V1 specified on the route R0 may be displayed side by side with the three-dimensional medical image M.

Further, although the shortest distance between the view point position P1 and the surface of a structure is used as the distance between the view point position P1 and the structure in the above-described embodiment, a distance between the view point position P1 and the centroid position of the structure may be used as the distance between the view point position P1 and the structure.

The above-described embodiment is provided by way of example only, and should not be used to construe that the entire description hereinabove limits the technical scope of the invention.

Besides the above-described embodiment, the technical scope of the present invention encompasses various modifications made to the system configuration, hardware configuration, flow of process, module configuration, user interface, specific contents of operations, etc., in the above-described embodiments without departing from the spirit and scope of the invention.

For example, with respect to the system configuration, although the modality 5 is directly connected to the image processing workstation 9 in the hardware configuration shown in FIG. 1 of the above-described embodiment, an image storage server may be connected to the LAN, and a three-dimensional medical image M formed by the modality 5 may be once stored in a database in the image storage server, and then the three-dimensional medical image M may be transferred from the image storage server to the image processing workstation 9 in response to a request from the image processing workstation 9.

Further, the endoscope 1 may not be a rigid endoscope, and a soft endoscope or a capsule endoscope may be used.

As the modality 5, an MRI apparatus, etc., may be used in place of the above-described CT apparatus or an ultrasound diagnostic apparatus.

Further, the part to be observed may not be the interior of the abdominal cavity, and may be another part of the subject, such as the interior of the thoracic cavity, which is suitable for endoscopic observation.

What is claimed is:

1. A virtual endoscopic image generation device comprising:
    a memory to execute executable instructions; and
    a hardware processor to execute the stored instructions, which when executed by the hardware processor cause the hardware processor to perform the following operations:
        obtain a three-dimensional image of a subject containing a plurality of structures;
        extract at least one structure from the three-dimensional image;
        determine a virtual view point position and a virtual direction of line of sight in a body cavity of the subject;
        store a display attribute defined for each of the plurality of structures, the display attribute defining an opacity that is changed depending on a distance from the virtual view point position; and
        change the opacity defined in the display attribute of the extracted structure depending on a distance between the virtual view point position and the extracted structure, and generating, from the three-dimensional image, a virtual endoscopic image containing the extracted structure having the display attribute with the changed opacity viewed from the virtual view point position in the direction of line of sight,
    wherein the opacity is chanced such that the opacity is 0 when the distance is equal to or greater than a first threshold value and equal to or smaller than a second threshold value, and the opacity is 1 when the distance is equal to a third threshold value between the first and the second threshold values.

2. The virtual endoscopic image generation device as claimed in claim 1, wherein the operation of changing the opacity includes calculating a shortest distance between the virtual view point position and the extracted structure.

3. The virtual endoscopic image generation device as claimed in claim 1, wherein the operation of changing the opacity includes calculating a distance between the virtual view point position and a centroid of the extracted structure.

4. The virtual endoscopic image generation device as claimed in claim 1, further comprising a display for displaying the virtual endoscopic image on a display unit.

5. A virtual endoscopic image generation method comprising:
    obtaining a three-dimensional image of a subject containing a plurality of structures;
    extracting at least one structure from the three-dimensional image;
    determining a virtual view point position and a virtual direction of line of sight in a body cavity of the subject; and
    changing, depending on a distance between the virtual view point position and the extracted structure, an opacity defined in a display attribute defined for each of the plurality of structures, the display attribute defining the opacity that is changed depending on a distance from the virtual view point position, and generating, from the three-dimensional image, a virtual endoscopic image containing the extracted structure having the display attribute with the changed opacity viewed from the virtual view point position in the direction of line of sight,
    wherein the opacity is changed such that the opacity is 0 when the distance is equal to or greater than a first threshold value and equal to or smaller than a second threshold value, and the opacity is 1 when the distance is equal to a third threshold value between the first and the second threshold values.

6. A non-transitory recording medium containing a program for causing a computer to carry out a virtual endoscopic image generation method, the method comprising:
    obtaining a three-dimensional image of a subject containing a plurality of structures;
    extracting at least one structure from the three-dimensional image;
    determining a virtual view point position and a virtual direction of line of sight in a body cavity of the subject; and
    changing, depending on a distance between the virtual view point position and the extracted structure, an opacity defined in a display attribute defined for each of the plurality of structures, the display attribute defining the opacity that is changed depending on a distance from the virtual view point position, and generating, from the three-dimensional image, a virtual endoscopic image containing the extracted structure having the display attribute with the changed opacity viewed from the virtual view point position in the direction of line of sight, wherein the opacity is changed such that the capacity is 0 when the distance is equal to or greater than a first threshold value and equal to or smaller than a second threshold value, and the opacity is 1 when the distance is equal to a third threshold value between the first and the second threshold values.

* * * * *